United States Patent
Haas et al.

(10) Patent No.: US 10,091,302 B2
(45) Date of Patent: Oct. 2, 2018

(54) SERVICE SYSTEM

(71) Applicant: MEDELA HOLDING AG, Baar (CH)

(72) Inventors: Matthias Haas, Oberrieden (CH); Beda Weber, Sins (CH)

(73) Assignee: MEDELA HOLDING AG, Baar (CH)

( * ) Notice: Subject to any disclaimer, the term of this patent is extended or adjusted under 35 U.S.C. 154(b) by 94 days.

(21) Appl. No.: 15/123,483

(22) PCT Filed: Mar. 4, 2015

(86) PCT No.: PCT/EP2015/054457
§ 371 (c)(1),
(2) Date: Sep. 2, 2016

(87) PCT Pub. No.: WO2015/132278
PCT Pub. Date: Sep. 11, 2015

(65) Prior Publication Data
US 2017/0078396 A1 Mar. 16, 2017

(30) Foreign Application Priority Data

Mar. 6, 2014 (EP) .................................. 14158098

(51) Int. Cl.
*H04L 29/08* (2006.01)
*A61M 1/06* (2006.01)
(Continued)

(52) U.S. Cl.
CPC ........... *H04L 67/12* (2013.01); *A61M 1/0023* (2013.01); *A61M 1/062* (2014.02); *G06F 19/00* (2013.01);
(Continued)

(58) Field of Classification Search
None
See application file for complete search history.

(56) References Cited

U.S. PATENT DOCUMENTS

| | | |
|---|---|---|
| 5,691,932 A | 11/1997 | Reiner et al. |
| 2003/0063135 A1 | 4/2003 | Liu |

(Continued)

FOREIGN PATENT DOCUMENTS

| | | |
|---|---|---|
| CN | 101111274 A | 1/2008 |
| DE | 10129621 A1 | 1/2003 |

(Continued)

OTHER PUBLICATIONS

International Search Report for application No. PCT/EP2015/054457, dated Jun. 11, 2015.

(Continued)

*Primary Examiner* — David Bilodeau
(74) *Attorney, Agent, or Firm* — Marshall, Gerstein & Borun LLP

(57) ABSTRACT

A service system in the field of collecting human breast milk or in the field of medical drainage has a base unit assigned to an individual or an entity and at least one mobile data medium. The mobile data medium can be brought by a user into data-communicating connection on the one hand with products in the field and on the other hand with the base unit. The base unit can be brought by the user into communicating connection with an external information and data platform. The system according to the invention offers optimal care and support of users in the field.

24 Claims, 12 Drawing Sheets

(51) Int. Cl.
*A61M 1/00* (2006.01)
*G16H 40/63* (2018.01)
*H04W 76/10* (2018.01)
*G06F 19/00* (2018.01)
*H04W 84/18* (2009.01)
*H04W 4/80* (2018.01)

(52) U.S. Cl.
CPC ......... *G16H 40/63* (2018.01); *H04L 67/1097* (2013.01); *H04W 76/10* (2018.02); *A61M 2205/3327* (2013.01); *A61M 2205/3584* (2013.01); *A61M 2205/3592* (2013.01); *H04W 4/80* (2018.02); *H04W 84/18* (2013.01)

(56) References Cited

U.S. PATENT DOCUMENTS

| | | | | |
|---|---|---|---|---|
| 2005/0101841 A9* | 5/2005 | Kaylor | ................ | G06F 19/3418 600/300 |
| 2009/0155753 A1* | 6/2009 | Ales | ................ | G09B 19/00 434/236 |
| 2010/0016789 A1* | 1/2010 | Bosshard | ................ | A61M 1/06 604/74 |
| 2010/0074058 A1 | 3/2010 | Campbell | | |
| 2010/0284251 A1 | 11/2010 | Chang | | |
| 2013/0093829 A1* | 4/2013 | Rosenblatt | ................ | G09B 5/00 348/14.01 |
| 2014/0378895 A1* | 12/2014 | Barack | ................ | A61M 1/064 604/74 |
| 2015/0265753 A1* | 9/2015 | Prentice | ................ | A61M 1/0031 604/74 |

FOREIGN PATENT DOCUMENTS

| | | |
|---|---|---|
| EP | 2218468 A2 | 8/2010 |
| GB | 2375181 A | 11/2002 |
| WO | WO-0045352 A1 | 8/2000 |
| WO | WO-01/47577 A2 | 7/2001 |
| WO | WO-03034254 A1 | 4/2003 |
| WO | WO-2009143093 A1 | 11/2009 |

OTHER PUBLICATIONS

English Translation of International Preliminary Report on Patentability for application No. PCT/EP2014/070695, dated Apr. 5, 2016.
Search Report for Chinese Application No. 201580012301.9, dated Mar. 21, 2018.

* cited by examiner

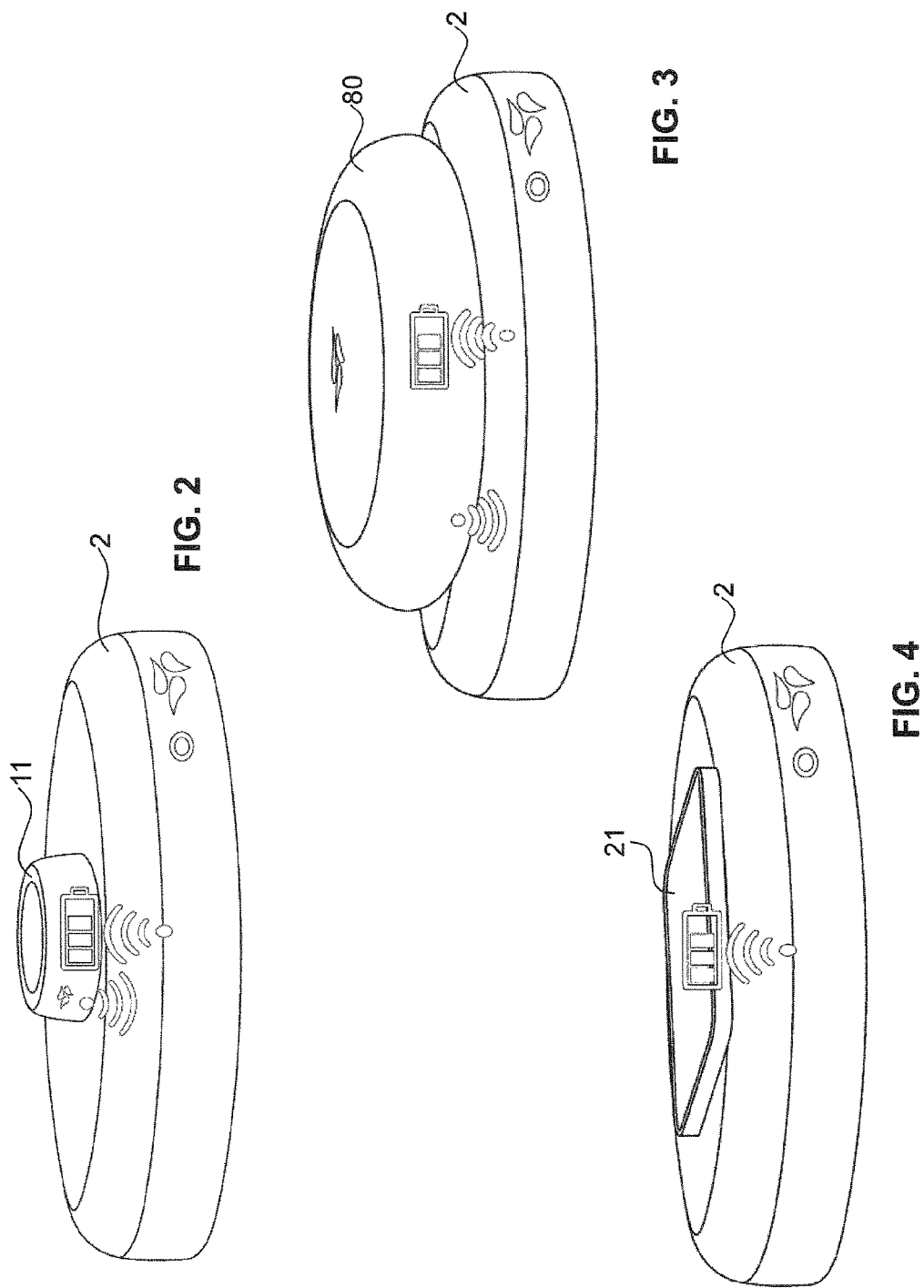

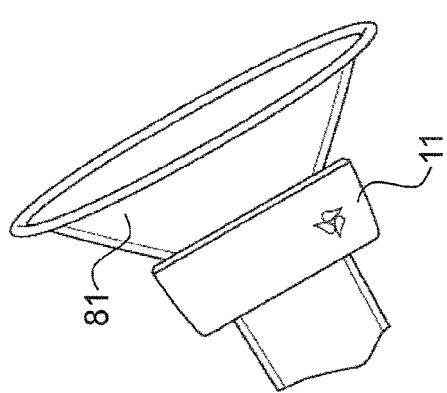
FIG. 7
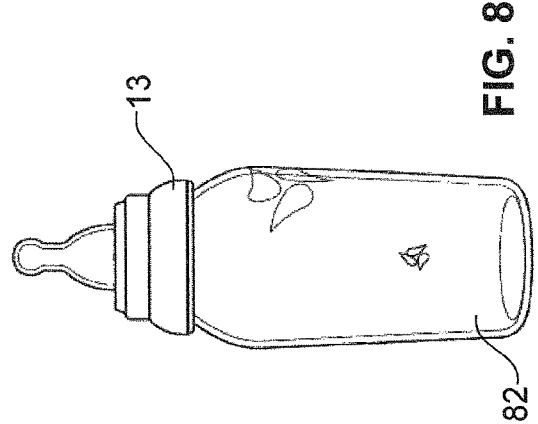
FIG. 8
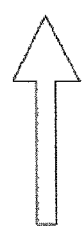
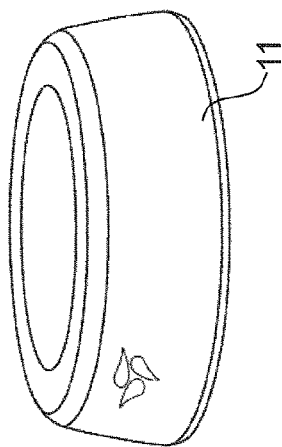
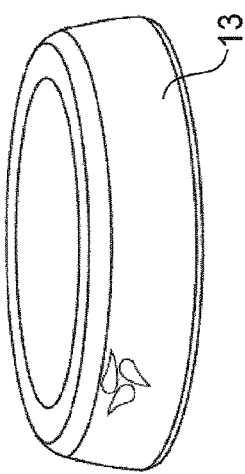

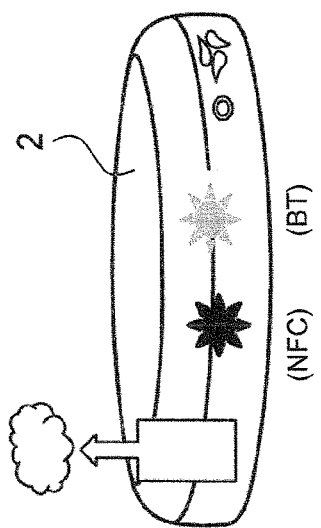
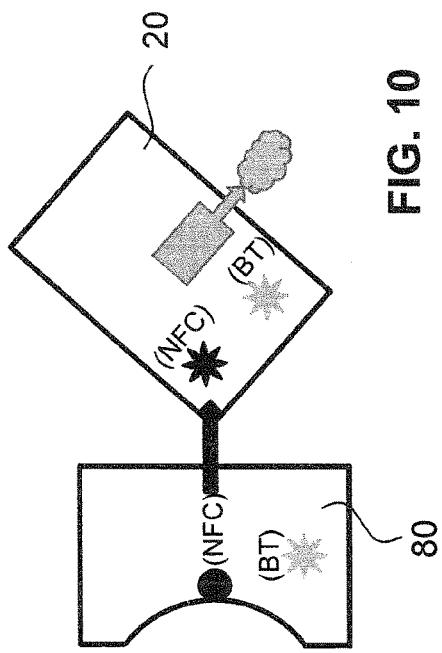
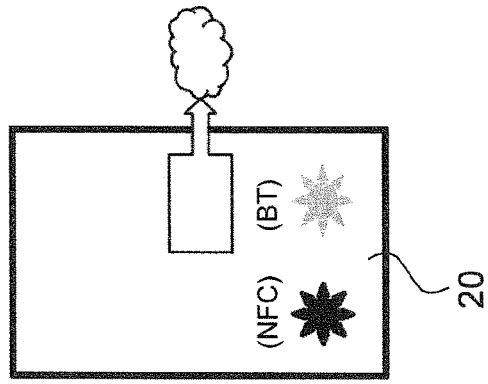
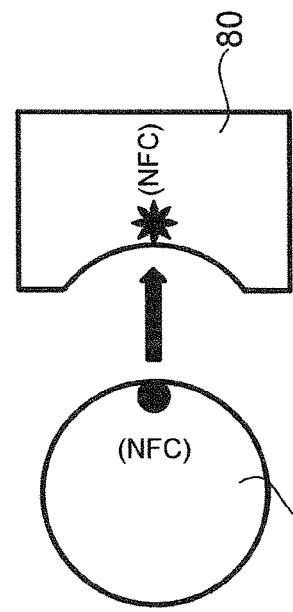
FIG. 9
FIG. 10
FIG. 11a

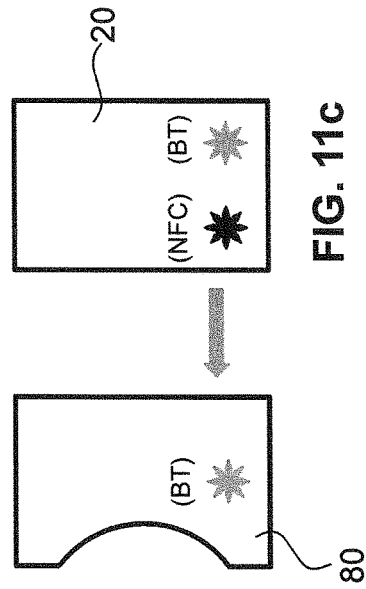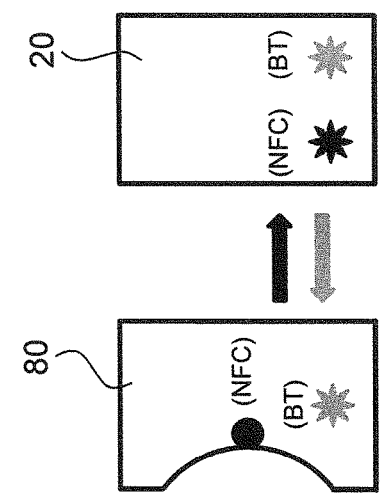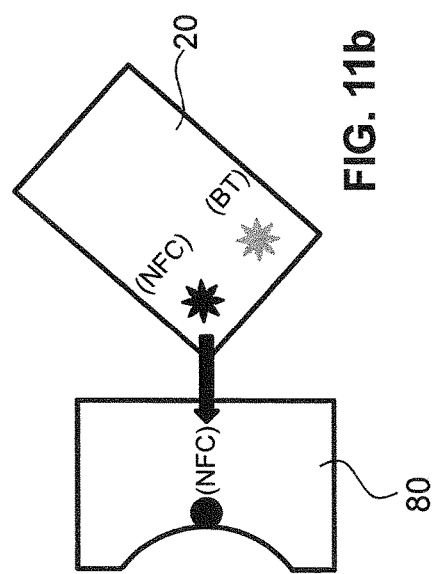

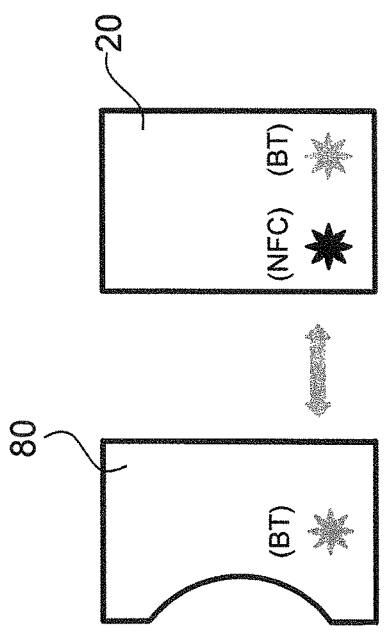
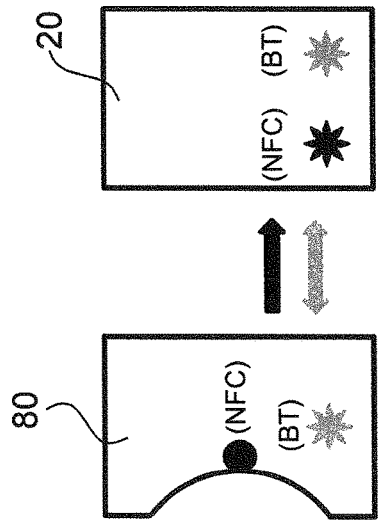
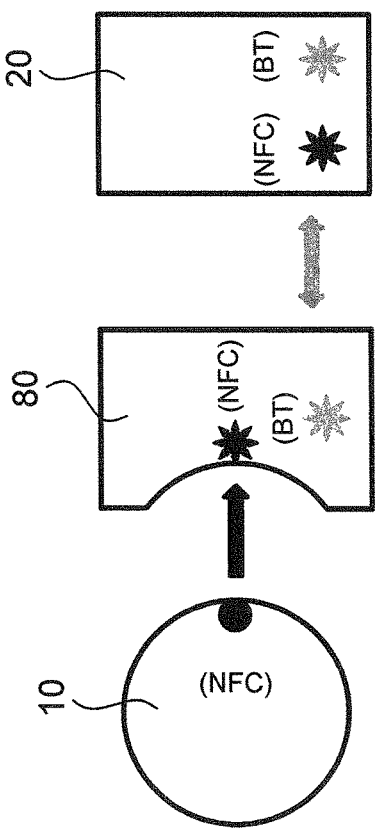
FIG. 12a
FIG. 12b
FIG. 12c

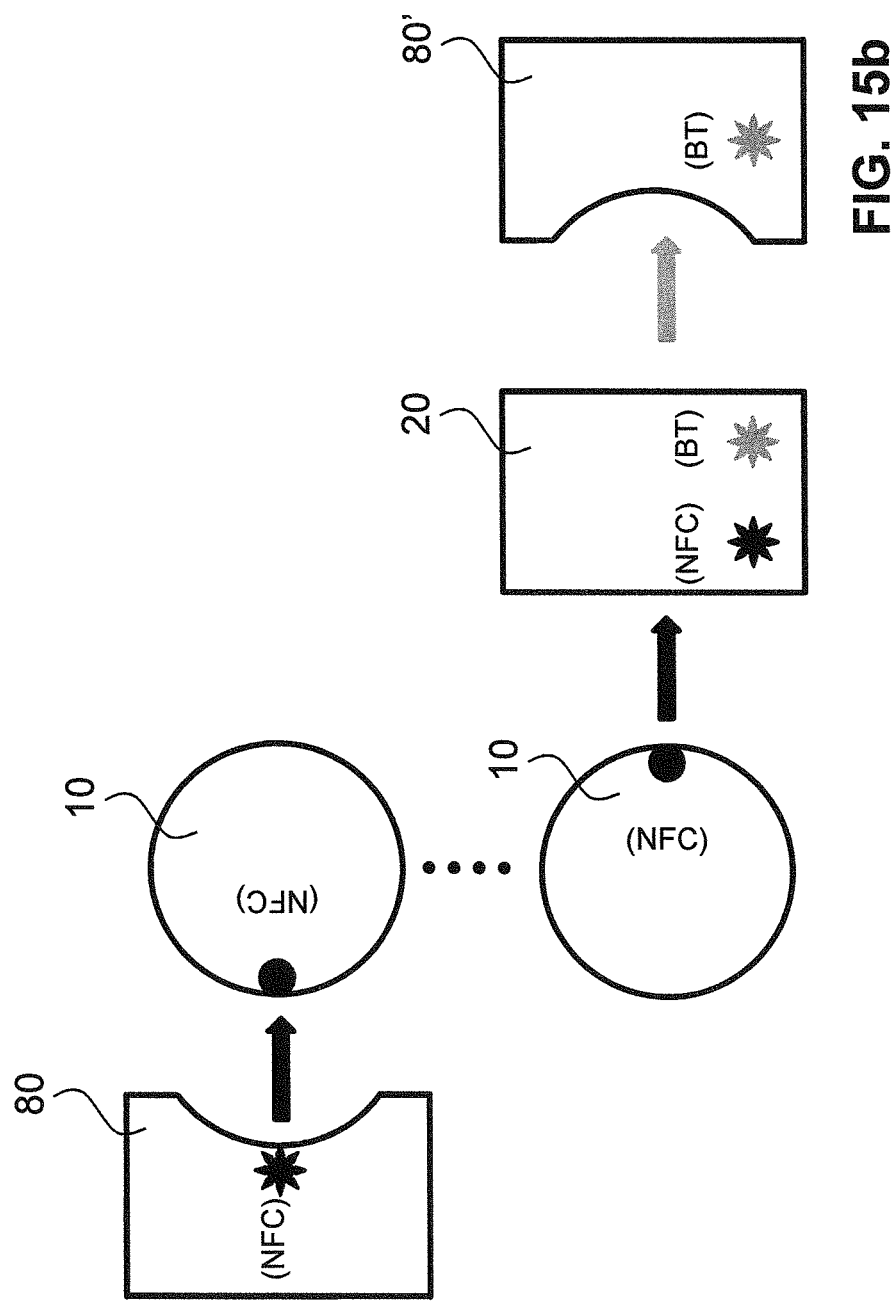

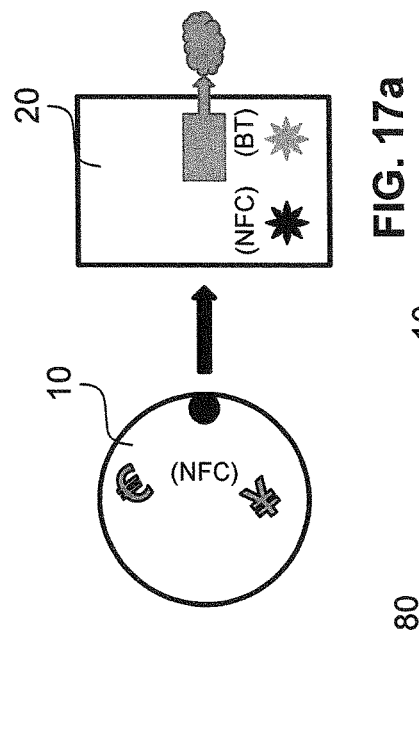
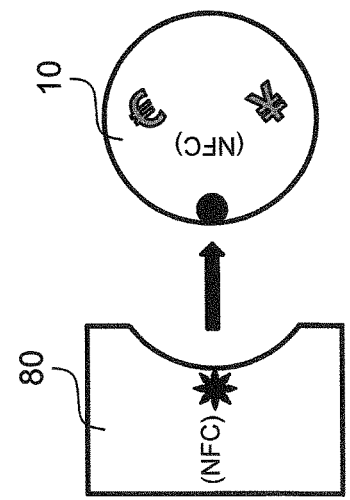
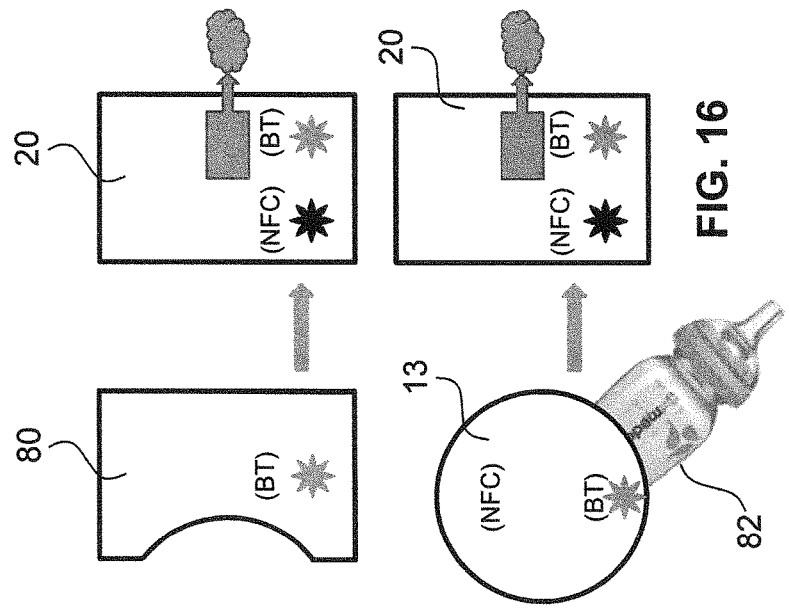

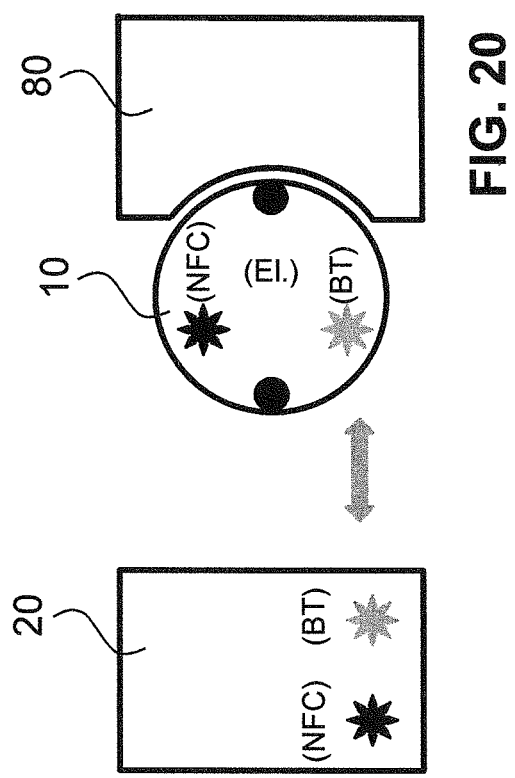

SERVICE SYSTEM

CROSS-REFERENCE TO RELATED APPLICATION

The present application is the US national phase of International Patent Application No. PCT/EP2015/054457, filed Mar. 4, 2015, which application claims priority to European Application No. EP 14158098.5, filed Mar. 6, 2014. The priority application, EP 14158098.5, is hereby incorporated by reference.

TECHNICAL FIELD

The present invention relates to a system in the field of collecting human breast milk or in the field of medical drainage, and to a base unit and a mobile data medium of such a system, and to a product, in particular a suction pump, for use in such a system. The system is suitable, in particular, for the area of breast pumps for pumping human breast milk as well as for thoracic drainage pumps and/or wound drainage pumps.

PRIOR ART

In the field of collecting human breast milk, as well as in the field of medical drainage, new discoveries have been made in recent years and a multiplicity of products in this field have been further developed or newly provided. In particular, suction pumps such as breast pumps, thoracic drainage pumps and wound drainage pumps have been greatly developed further in recent years.

For instance, WO 01/47577 discloses a breast pump which has different suction curves that differ from one another not only in frequency and maximum reduced pressure. Furthermore, the user can provide the controller of the pump with new suction curves. This breast pump is known on the market by the name "Symphony".

Attempts are furthermore being made to achieve new discoveries about the provision of breast milk in the breast as well as the drinking behaviour of babies, and to incorporate these discoveries into the further development of breast pumps, breast shields, teats and baby bottles. These discoveries are based essentially on a mixture of empirical values and scientific research. The optimum, however, respectively depends on the mother and baby, and therefore differs individually. The same also applies to medical drainage, in particular for thoracic drainage and wound drainage.

Although devices such as breast and drainage pumps are usually provided with operating instructions and recommendations for their use, the increasing incorporation of a plurality of operating parameters and further variables makes optimal adjustment of the devices by the end user, for example the mother, often impossible or unrealistic. Often, moreover, a full overview by the manufacturer about the individual requirements and the capacity for individual optimization by the user is lacking.

In the prior art, various systems which deal with individual data acquisition regarding pregnancy, birth and the first months of the baby's life are furthermore known.

For instance, WO 2009/143093 discloses a system for acquiring lactation data from a mother, these data together with other medical information about the mother being stored in a database.

In WO 03/034254, medical data are collected before, during and after pregnancy and made available in a watch. Also, WO 00/45352 provides a data memory in which medical data from birth are stored. In GB 2 375 181, data about the development of the baby are collected and an automatic assessment of the status of the baby is provided.

DE 101 29 621 and US 2010/0074058 disclose watches as guidance aids for feeding babies. US 2010/0284251 also relates to a management system for giving food to babies. US 2003/0063135 and U.S. Pat. No. 5,691,932 also take into account other aspects of baby care in the management system.

Although these apparatuses help mothers and advisers of mothers to observe the development of the child and find a daily routine which is as regulated as possible, they do not provide mothers with any help in the selection and use of products available in the field of breastfeeding or collecting breast milk.

Also in the field of medical drainage, in particular thoracic drainage and wound drainage, corresponding assistance for the medical personnel and patients is lacking.

SUMMARY OF THE INVENTION

It is therefore an object of the invention to provide a system in the field of collecting human breast milk or in the field of medical drainage, which allows optimum use of available products.

This object is achieved by a system having the features of Patent claim 1, by a base unit having the features of Patent claim 14, a mobile data medium having the features of Patent claim 15 and a product for use in such a system, having the features of Patent claim 18.

The service system according to the invention has a base unit assigned to an individual or an entity, and at least one mobile data medium. The mobile data medium can be brought by a user into data-communicating connection on the one hand with products in the field of collecting breast milk or in the field of medical suction pumps and on the other hand with the base unit, and the base unit can be brought by the user into communicating connection with an external information and data platform.

Products in the sense of this text are, in a first embodiment, purchasable or hireable devices, apparatuses and articles from one or more manufacturers.

In another embodiment, as an alternative or in addition, products are commercially or freely offered services, for example lactation advice or baby feeding advice. Further embodiments additionally involve yet other types of products.

In the case in which the system is used in the field of breastfeeding and the suction pump is a breast pump, the individual is a mother who will be breastfeeding or breast pumping, or who is already doing so, or the baby. In this case, the entity may for example be a hospital, a birthing centre, a baby unit or a neonatal unit of a hospital, a lactation consultancy with a plurality of mothers to be advised, or another institution active in the field of advice. The user is an end user, for example the mother, care personnel, doctors, lactation consultants or other persons assisting the mother with the care of the baby.

In the case that the system is used in the field of medical drainage, particularly thoracic drainage or wound drainage, the individual is a patient. The entity is again a hospital or a care institution, or a department of the hospital or of the institution. The user is preferably a doctor or the care personnel. They may, however, also be the patient or a person caring for the patient, for example.

In a preferred embodiment, the mobile data medium can be brought by the user into data-communicating connection with one or more of the following products: breast pumps, breast shields, teats, milk collection containers, milk storage containers, milk delivery containers, vacuum tubes, plug connections. In another embodiment, as an alternative or in addition, the mobile data medium can be brought into data-communicating connection with one or more of the following products: thoracic drainage pumps, fluid collection containers, drainage and service tubes, plug connections. In another embodiment, as an alternative or in addition, the mobile data medium can be brought into data-communicating connection with one or more of the following products: wound drainage pumps, wound coverings, drainage tubes, service tubes, plug connections.

Preferably, the mobility of the mobile data medium is independent of the base unit and/or of the products, so that the user, in particular the individual, can always carry the data medium with him or her.

The mobile data medium may remain with the individual, so that he or she can try alternative devices and apparatuses, in particular new suction pumps, and these can be operated from the start on the basis of data from previous experience with suction pumps or devices. In this way, more rapid and simpler optimization of the operating parameters of the new suction pump, or of the new apparatus, is possible. When leaving hospital, for example, a mother may receive a mobile data medium on which all relevant data of the breast pump used in the hospital are stored, for example the breast pump type and the adjusted suction parameters, including the selected suction curve if applicable. If she now wishes to hire or purchase her own breast pump, this makes it easier for her to select and start to use the pump, even if she does not purchase or hire the same model as used in the hospital.

When the mother leaves the hospital, individual amounts of milk and pumping intervals and pumping durations may also be stored on the mobile data medium. This also helps in selecting the pump. They are, moreover, also useful data for the lactation consultant who undertakes the further care of the mother.

All these data are also helpful during the hospital stay for the specialist personnel, or when using a different suction pump in the hospital. Particularly in the case of premature babies or in the case of sick or handicapped children, these data may also comprise information for treating the pumped breast milk.

A plurality of mobile data media may be assigned to the mother or the baby. In particular, first data media may relate to the breast pump and second data media to other products. The other products may for example be an accessory, for example a milk collection container, a breast shield, a teat or a milk delivery bottle, i.e. a breastfeeding bottle. The data for all these devices and apparatuses may, however, also be stored on the same data medium.

These data stored on the at least one mobile data medium are transmitted to the base unit and/or further data reach the mobile data medium from the base unit. Thus, in the case of a plurality of data media assigned to the same individual, data and information can be exchanged, optimized and also converted. If, for example, a larger breast shield is used, then pumping parameters in the suction pump may be automatically altered. If the base unit is assigned to an entity having a plurality of individuals, then empirical values of particular individuals may also be made accessible to other individuals.

The base unit according to the invention is connected to an external information and data platform. The platform may be present locally in a hospital, a care institution or another similar facility. Preferably, however, it is Internet-based, at least individual parts of it preferably being placed in a cloud. The platform, however, may also be located exclusively at a product manufacturer. By means of this platform, data can be exchanged between individuals or entities and advisers or manufacturers, these data can be optimized on an individual-related or cross-individual basis and converted, and transmitted again or assigned to individual base units.

Via this platform, for example, a mother may seek help from a lactation consultant, receive help from the manufacturer in the event of a malfunction of the pump, or she may be protected against purchasing incorrectly when ordering consumable material. Furthermore, advisers and manufacturers may obtain practical experience from the data pool and draw conclusions for advice and further development of products. In the event of a suboptimal outcome when using the products, the system therefore offers the fastest possible identification and optionally solution of the problem.

Another advantage is that the customer loyalty is increased in all fields, in particular as regards products in the field of breastfeeding. The mother may already receive a data medium before the birth, so that she can become acquainted and comfortable beforehand with the data and information platform and/or can also identify the products in corresponding specialist shops with the data medium.

In a preferred embodiment, therefore, the mobile data medium allows bidirectional data transfer with the base unit, in order to permit at least some of the functions mentioned above.

Preferably, the data communication between the mobile data media and the base unit and/or between the mobile data media and the products, in particular the suction pumps, takes place wirelessly. This facilitates handling.

In one embodiment, the base unit is an independent unit with an Internet connection function. It may, however, also be part of a multifunctional communication means, for example a smartphone. For example, an app may be downloaded onto the smartphone so that the communication with the mobile data medium and/or the external platform can already take place before purchase or hiring of any apparatuses and devices.

Preferably, the base unit allows bidirectional information and data transfer with at least one region of the information and data platform, so that at least some of the functions described above can be carried out.

Preferably, the base unit can be brought by the mother or by the user into data-communicating connection with the products, in particular the suction pumps. If the connection is bidirectional, not only can information and data be downloaded from the products, in particular the suction pumps, but also new information, data, operating parameters and operating programs can be loaded into the products, in particular into the suction pumps. In particular, it is possible to use suction curves newly developed by the platform via the operating unit, or other new data, information, parameters or programs obtained subsequently by the user and/or downloaded from the platform.

Preferably, the base unit has a support surface for supporting the mobile data medium for the purpose of data transfer. In this way, for example, energy storage units of the data medium, of the products, in particular of the suction pumps, and of a smartphone, inter alia, can also be charged wirelessly.

The mobile data medium preferably has the external shape of a gaming chip, a coin or a credit card. In these embodiments, it is relatively inexpensive and small and can be kept anywhere, particularly in a handbag or trouser pocket. It may, however, also be removably arranged or integrated in a fixed way in or on the product itself. Furthermore, a smartphone or another multifunctional communication means may form the mobile individual data medium.

In one embodiment, the mobile data medium has at least one sensor for the detection of measurement values. In this way, particularly when using a milk collection container or a milk delivery container, it may be used to detect and/or measure the amount of milk entering or flowing out of the container, and/or the temperature.

Preferably, the mobile data medium is formed for fastening on a product for the purpose of data-communicating or measurement value-detecting connection. Correspondingly, the product, in particular the suction pump, is formed in order to receive the mobile data medium for the purpose of data-communicating or measurement value-detecting connection.

Further embodiments are specified in the dependent claims.

BRIEF DESCRIPTION OF THE DRAWINGS

Preferred embodiments of the invention will be described below with the aid of the drawings, which merely serve for explanation and are not to be interpreted as restrictive. In the drawings:

FIG. 2 shows a schematic representation of a base unit according to the invention with a mobile data medium placed thereon;

FIG. 3 shows a schematic representation of a base unit according to the invention with a breast pump placed thereon;

FIG. 4 shows a schematic representation of a base unit according to the invention with a smartphone placed thereon;

FIG. 7 shows a third combination of the data medium according to the invention with a breast shield;

FIG. 8 shows a fourth combination of the data medium according to the invention with a baby bottle;

FIG. 9 shows a schematic representation of two base units;

FIG. 10 shows a first application possibility according to the invention of a suction pump with a base unit;

FIG. 11a shows a second application possibility according to the invention of a suction pump with a data medium;

FIG. 11b shows a variant of the application possibility according to FIG. 11a in the combination of a suction pump with a base unit;

FIG. 11c shows a variant of the application possibility according to FIG. 11a in the combination of a suction pump with a base unit;

FIG. 11d shows a variant of the application possibility according to FIG. 11a in the combination of a suction pump with a base unit;

FIG. 12a shows a third application possibility according to the invention of a suction pump with a base unit;

FIG. 12b shows a variant of the application possibility according to FIG. 12a in the combination of a suction pump with a base unit;

FIG. 12c shows a variant of the application possibility according to FIG. 12a in the combination of a suction pump with a base unit and a data medium;

FIG. 15b shows a variant of the application possibility according to FIG. 15a;

FIG. 16 shows a seventh application possibility according to the invention of a suction pump with a base unit and a data medium;

FIG. 17a shows an eighth application possibility according to the invention of a data medium with a base unit;

FIG. 17b shows a variant of the application possibility according to FIG. 17a;

FIG. 18b shows a variant of the application possibility according to FIG. 18a;

FIG. 19b shows a variant of the application possibility according to FIG. 19a; and FIG. 20 shows an eleventh application possibility according to the invention of a suction pump with a base unit and a data medium.

DESCRIPTION OF PREFERRED EMBODIMENTS

Figure 1:
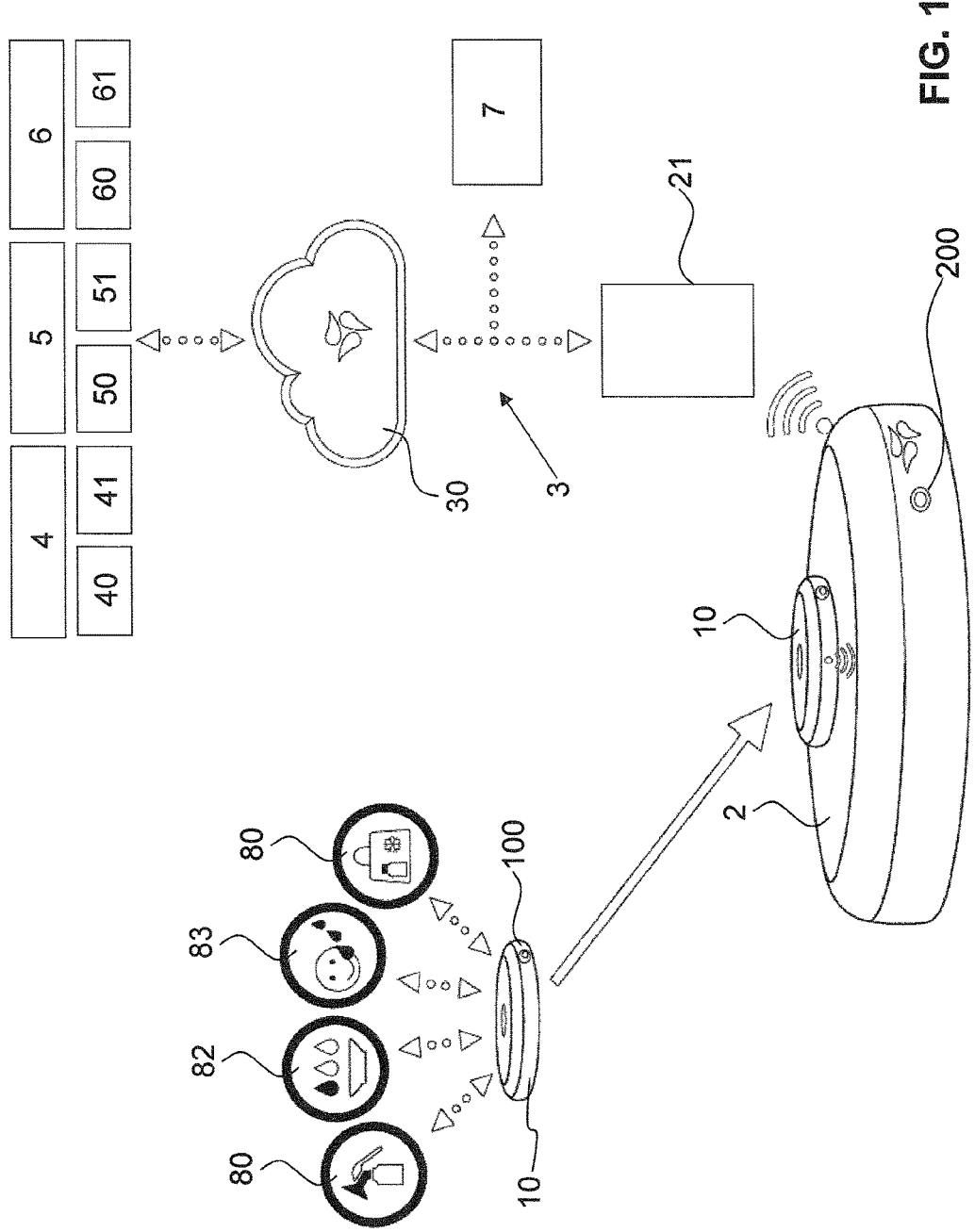
FIG. 1 shows a schematic representation of the system according to the invention in the field of collecting human breast milk.

FIG. 1 schematically represents a service system according to the invention in the field of collecting breast milk. The comments made here may, however, be applied similarly to the field of medical drainage, in particular thoracic drainage and wound drainage.

The system has at least one mobile data medium 10, also referred to below as a chip, and at least one base unit 2. Preferably, the system comprises a plurality of base units 2 and a plurality of chips 10.

The data medium 10 is formed in this example in the shape and size of a flat round gaming chip. It may, however, also have other sizes and shapes. Preferably, it is made to be lightweight, robust and small, so that it can be placed in a trouser pocket or a purse. It may also be formed as a chain, whether for example for a keyring or for a necklace.

The mobile data medium 10 has a data memory and the possibility of active and/or passive data transmission. A microprocessor having few combination and evaluation possibilities is preferably likewise provided. The mobile data medium 10 thus has no intelligence, or only low intelligence.

As schematically represented in FIG. 1, the data medium 10 can be brought into data-communicating connection with various products. These products are, for example, a manual or motorized breast pump 80, a milk collection container 82 or a milk delivery unit 83. It is also possible that the same data medium 10 can be brought into communicating connection with all these products, but preferably in succession. The unidirectional or bidirectional (that is to say taking place in one or two directions) communication with the products preferably takes place wirelessly with conventional known means.

The data medium 10 preferably has at least one display, here an optical display, for example a light-emitting diode or an LCD 100, which indicates for example by flashing or constant shining that data transfer is taking place, or that it is completed.

Depending on the application field of the data medium 10, it may furthermore be equipped with an energy storage unit. The energy storage unit is preferably rechargeable.

The mobile data medium 10 is assigned to an individual. In the field of collecting breast milk, the individual is usually a mother or a baby. Assignment may take place purely by the chip 10 being in the possession of the individual. Individual-specific identification data may be stored on the chip 10, although it must not. The chip 10 may, for example, also be assigned merely by means of a chip-specific identification code. The chip 10 may furthermore be assigned to a mother or a baby, but be in the possession of a helper assisting the mother in the care, for example the father or a nurse. The users are therefore not only mothers, but also other persons.

The users receive the chips 10 in various ways. For instance, a chip, or a plurality of such chips, may already be given to a mother during the maternity care. She may receive it during the hospital stay for the birth, or when leaving hospital. She may also receive it from a seller of field-specific products, from a doctor or a lactation or baby nutrition consultant.

In the field of drainage, the individual is similarly a patient, and the users are patients, doctors, care personnel, relatives and acquaintances. Usually, but not exclusively, the chip is received from the hospital, the care institution or the doctor.

The use of the chip 10 will be described later in the text.

The system according to the invention also comprises at least one base unit 2. This base unit 2 is assigned to an individual or an entity. The individual has already been described above. The entity is usually a hospital or a care or advice institution, in particular a lactation consultancy. The entity looks after a plurality of individuals who have the aforementioned mobile data medium 10.

The base unit 2 is usually static, and is usually small enough to be transported from one location to another. The base unit 2 preferably has an Internet connection in order to communicate with an external information and data platform 3 and exchange data as well as information. The base unit 2 may usually communicate unidirectionally or bidirectionally with a multiplicity of chips 10, i.e. interrogate and/or receive data of the chips. In particular, it is capable of identifying the chips 10 and assigning them to the individual.

The base unit 2 preferably has a data memory for storing data from the chips 10, but also from the information and data platform 3. The base unit 2 preferably also has at least one display, here a light-emitting diode or LCD 200, in order to display the communication and/or completion of the data transfer. Here again, the unidirectional or bidirectional communication with the chips 10 preferably takes place wirelessly via known means.

The unidirectional or bidirectional communication with the information and data platform 3 may take place wirelessly or via a cable connection. It is also possible to use a connection unit 21 for this, for example a smartphone. The base unit 2 preferably has greater intelligence than the chips 10, i.e. it can for example identify, select, group, modify and reassign chips and data.

In FIG. 2, a mobile data medium in the form of a data medium ring 11 is placed on a surface, preferably a support surface with an integrated sensor, of the base unit 2, and transmits and receives data.

The base unit 2 can preferably also be brought into unidirectional or bidirectional data-communicating connection with the products. This is represented in FIG. 3. A breast pump 80, here a compact portable breast pump, rests on the aforementioned contact surface of the base unit 2, and transmits and receives data.

FIG. 4 represents that the base unit 2 is transmitting data to a connection unit 21, here a smartphone.

In all three cases according to FIGS. 2 to 4, in a preferred embodiment an energy storage unit of the resting element is also charged by means of the base unit 2. This makes sense in particular when the base unit 2 itself is connected to the electricity mains.

In all these cases, by placing the element on the base unit, the user determines whether and when the data and information are transmitted. This transmission of the data and information may take place automatically and/or by special activation, depending on the embodiment.

As represented in FIG. 1, the information and data platform 3 is preferably at least partially located in a cloud 30. Clouds have by now become well-known IT infrastructures which are provided via a network, while being dynamically adapted to requirements. Various circles have access to this cloud according to the invention 30: on the one hand the various base units 2, a single base unit 2 being represented symbolically for all of them in FIG. 1. Furthermore, product employers, or users, 4 have access, for example mothers 40 and their helpers 41, in order to query data and information and load data and information onto the platform 3. Support units 5, such as hospitals, care units, lactation consultancies 50 and other advisory services 51 can load information and data from the platform 3 and enter data and information into the platform. Manufacturers 6, or their customer services 60 and internal departments 61, such as marketing, quality assurance, customer support and development departments, can also use the system bidirectionally. The platform 3 may furthermore be in communication with, or contain, one or a plurality of electronic points of sale 7 (e-shops). Other circles may likewise receive unidirectional or bidirectional access, for example research institutes or universities.

In the platform 3, data are exchanged, converted, optimized or reassigned to individual base units. Other individual circles may likewise receive, automatically or on request, data and information modified in this way. Furthermore, the platform 3 is used for direct and simplified exchange between a particular individual or entity and another circle, or between individuals or entities. This will also be explained in more detail below.

Figure 5:
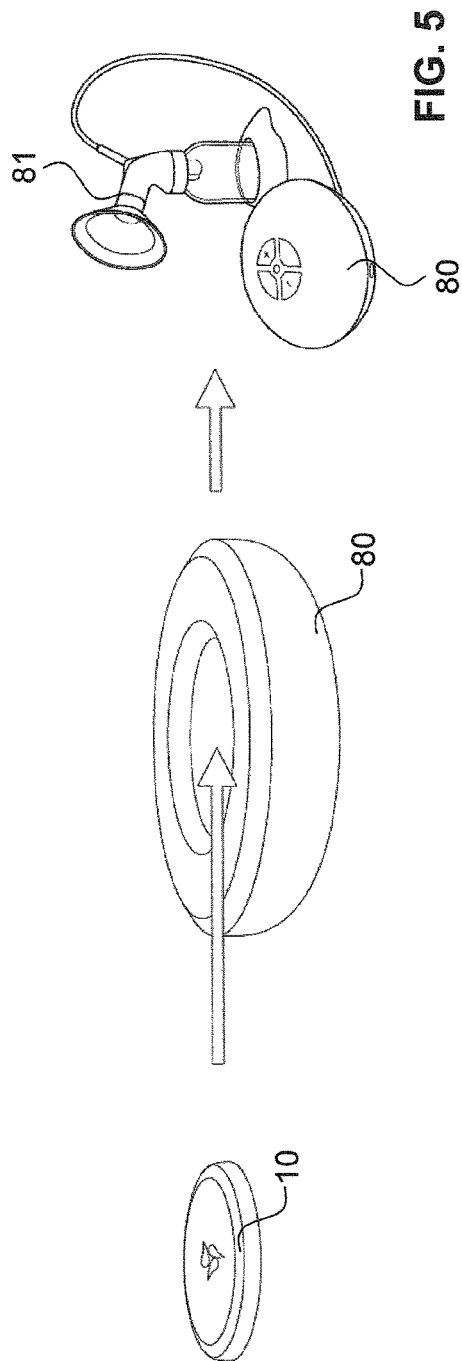
FIG. 5 shows a first combination of the data medium according to the invention with a breast pump.

FIG. 5 represents a possible configuration of a chip 10 and breast pump 80. The chip 10 is round and flat like a coin, and the breast pump 80 has a corresponding indentation. Possible data transfers will be described below.

Figure 6:
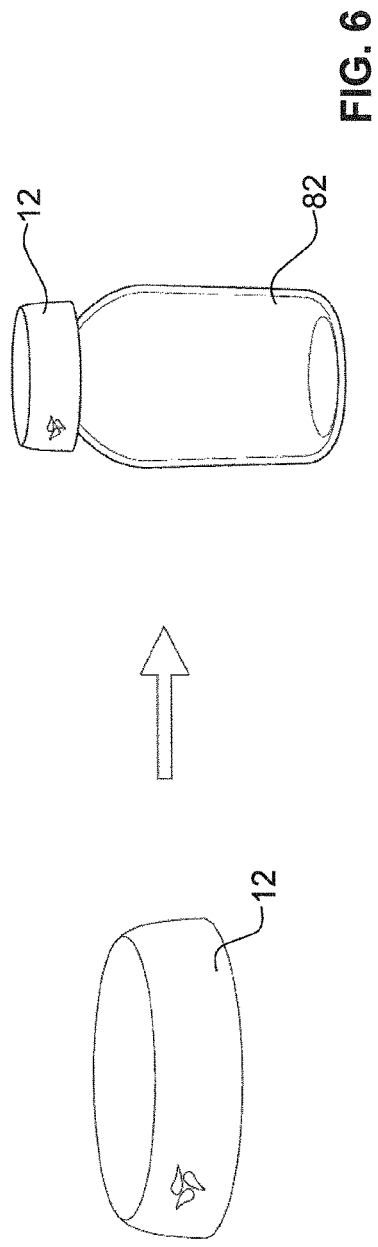
FIG. 6 shows a second combination of the data medium according to the invention with a milk collection container.

In FIG. 6, the mobile data medium 10 is configured in the form of a lid for a milk collection container 82, here in the form of a bottle. The data medium 10 preferably contains data regarding the filling time, possibly also the filling quantity or the temperature. As an alternative or in addition, it may contain data and information concerning treatment of the milk for the purpose of administering it. These data may be transmitted to the base unit 2, but also to a product, for example a milk delivery bottle or a milk warmer.

In FIG. 7, the mobile data medium 11 is a ring, which can be placed on a breast shield 81. Conventionally, the breast shields 81 have a funnel to be placed on the mother's breast and a subsequent cylindrical part. The data medium 11 can be slid over this cylindrical part and bear on the funnel. By means of sensors in the data medium ring 11 or in the breast shield itself, it is possible to detect the amount of milk pumped and these data can be transmitted to the base unit or to one of the products. If the sensor is in the breast shield, the data are first transmitted to the ring 11. The data medium ring 11 preferably has an energy storage unit in this case.

FIG. 8 likewise represents a data medium in the form of a ring 13. It may be the same ring as in FIG. 7, or one constructed in a different way. In this case, it is used with a baby bottle 82. It measures the flow of milk leaving the bottle, or the amount of milk leaving the bottle. To this end, the sensor may be arranged in the data medium, in the bottle or in the teat. Here again, the ring 13 preferably has an energy storage unit.

Some application examples will be explained with the aid of the figures described below. There are other application possibilities. The application examples may preferably be implemented in a single embodiment of the system according to the invention. In other embodiments of the system, however, only one of these possibilities, or subcombinations, is implemented.

In FIG. 9, it is represented that the base unit 2 on the one hand may be a separate part, or it may also be integrated in a smartphone 20 or in another multicommunication device, for example an app. The mobile data medium may also either be integrated in a product or implemented in a smartphone or another multicommunication device, for example likewise as an app.

The subsequent figures respectively represent a smartphone 20, the disclosure below being applicable in the same way to other base units. Furthermore, a breast pump is primarily explained as the product. The types of communication and the applications may also be applied to other products.

FIG. 10 shows a first application: the breast pump 80 is equipped with an NFC tag (near-field communication tag). By means of the smartphone 20, manufacturer data are read out and stored individual-specifically. The data may be transmitted via the Internet to the cloud, and thus communicated to the manufacturer or another circle.

In FIG. 11a, the chip 10 has individual-specific data for optimized pumping. The breast pump 80 has an active NFC tag reader, in order to read these data from the chip 10.

In FIG. 11b the breast pump 80 is equipped with an NFC tag, so that it can receive data from the smartphone 20.

In FIG. 11c, the pump 80 is equipped with a Bluetooth module (BT) and communicates with the smartphone 20, so that the smartphone 20 can transmit data and information to the pump 80.

In FIG. 11d, the pump 80 has a passive NFC tag and a Bluetooth module. The NFC tag configures a smartphone 20 app, which in turn configures the pump via Bluetooth.

In these examples according to FIGS. 11a to 11d, the pump is configured with the user. For example, optimal operating parameters for the individual or optimized programs are loaded, or generally newly developed programs and/or operating parameters are installed. The user can therefore provide an existing pump with new and/or improved, or optimized, functions.

In the embodiments according to FIGS. 12a to 12c, data exchange takes place between the pump 80 and the smartphone 20. In FIG. 12a, the pump 80 is equipped with a Bluetooth module and thus communicates with the smartphone 20. In FIG. 12b, the pump 80 has an NFC tag and a Bluetooth module. The NFC tag configures a smartphone app, which in turn communicates with the pump 80. In FIG. 12c, the pump 80 is equipped with an active NFC reader/writer and a Bluetooth module. The Bluetooth connection is configured by means of NFC, and the smartphone 20 then communicates with the pump 80.

Figure 13:
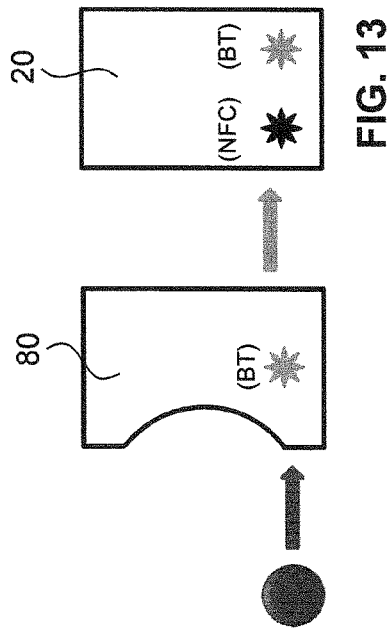
FIG. 13 shows a fourth application possibility according to the invention of a suction pump with a base unit.

In FIG. 13, an amount of milk produced is recorded. The pump 80 or the milk collection container, or an associated data medium, measures the amount of milk produced, or has these data in another way, for example by manual input. These data are transmitted to the smartphone 20. In this case, the transmission takes place via the pump 80. As claimed above, they may also be transmitted via other products or the data medium.

Figure 14:
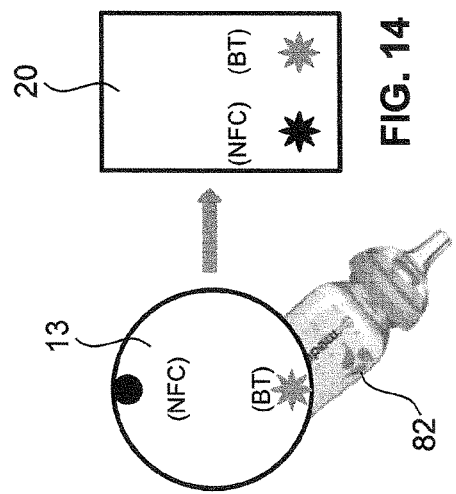
FIG. 14 shows a fifth application possibility according to the invention of a suction pump with a data medium.

In FIG. 14, the amount of milk delivered is recorded, for example as described in FIG. 8, and transmitted to the smartphone 20.

The data transmitted according to FIGS. 13 and 14 may be entered and managed in a common individual-specific diagram or a common individual-specific list in the base unit, but as an alternative or in addition also on the platform 3. If data of the same individual are transmitted via various base units 2, then the platform 3 makes it possible to combine these data in a common diagram or in a common list. This list, or this diagram, allows versatile conclusions and instructions for further procedure. It is also possible in this way to combine data of a plurality of individuals and provide instructions therefrom for particular individuals or other circles.

Figure 15A:
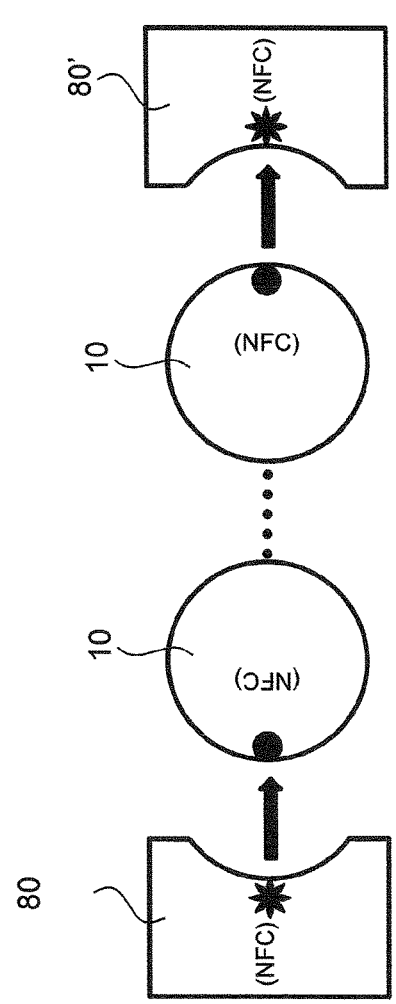
FIG. 15a shows a sixth application possibility according to the invention of a suction pump with a data medium.

In FIGS. 15a and 15b, data transfer takes place from the hospital to the house. That is to say, an individual who has already collected data in the hospital and, for example, has found an optimal breast pump adjustment, can take these data home with her in order to likewise optimally use the products there. In FIG. 15a, adjustments of the hospital pump 80 and/or other data and information are stored on the mother's chip 10 by the hospital pump 80 or the base unit in the hospital. At home, these data can then be transmitted to the individual pump 80' or to other of the mother's products. As an alternative or in addition, the same data may also be transmitted at home into the mother's individual base unit 20 by means of the chip 10. The data transfer to the product, in particular to the pump 80', may also take place via this base unit 2. This is represented in FIG. 15b.

In FIG. 16, the system allows optimized reordering of replacement material. The product, here the pump 80, and/or the chip 10 knows which replacement parts are available for the corresponding product. By means of a smartphone 20 and app installed thereon, the desired replacement parts can be ordered from the e-shop 7. Incorrect ordering is thus avoided.

In FIGS. 17a and 17b, a bonus program is proposed. The chip 10 according to FIG. 17a is loaded with a credit balance which can be redeemed by means of the base unit, here again the smartphone 20, in the e-shop. This, for example, makes gift vouchers possible. In FIG. 17b, a credit balance on the chip 10 is increased by use of the product, here the breast pump 80. This can also subsequently be redeemed.

Figure 18A:
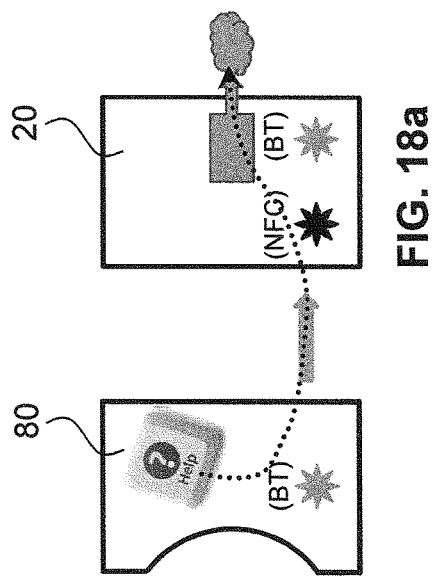
FIG. 18a shows a ninth application possibility according to the invention of a suction pump with a base unit.
Figure 18B:
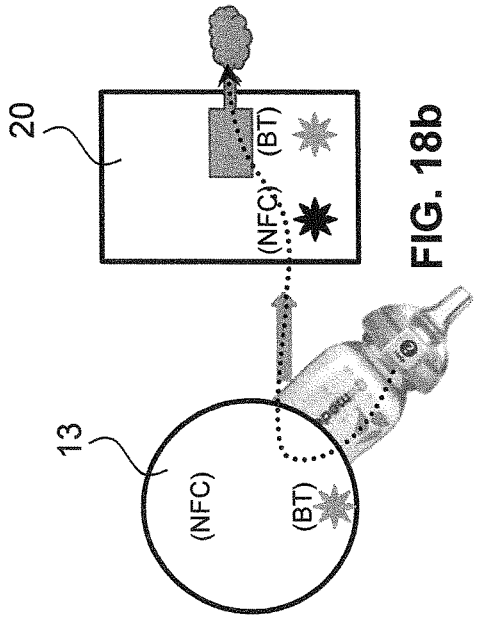
Figure 19A:
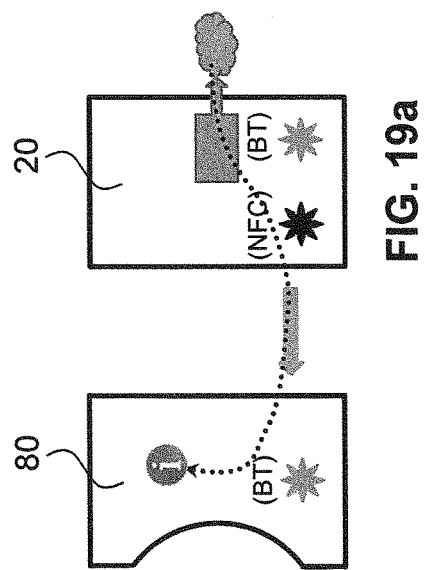
FIG. 19a shows a tenth application possibility according to the invention of a suction pump with a base unit.
Figure 19B:
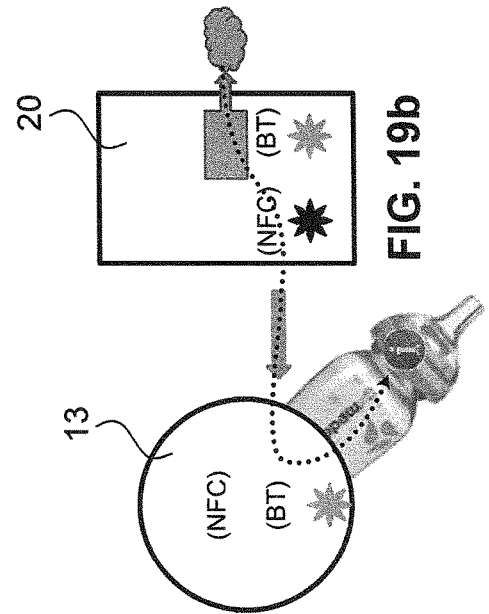

In FIGS. 18a and 18b, signals can be transmitted from the product 80, 82 to the base unit, here the smartphone 20, and from there to the platform 3. This is advantageous in particular when problems occur with the user. A point of advice or a customer service can thus receive signals directly from the product and check where the error might lie. To this end, the manufacturer or other circles on the platform 3 may provide corresponding information tools or automatic error detection tools. According to FIGS. 19a and 19b, subsequently, or even proactively, user support may be provided by the point of advice, a customer service or other circles, this support directly influencing the product, here the pump 80, or the chip 10, or such transmitted information being displayed directly on the product.

FIG. 20, represents an upgrade of a product, so that it can actually take part in the system according to the invention. The chip 10 is provided with a corresponding upgrade option, which by contact with the pump 80 or another product allows communication thereof with the smartphone 20 and therefore the platform 3. This chip 10 communicates with the product preferably via an electrical interface, and therefore preferably remains with the product.

The system according to the invention offers optimal care and support of users in a special field.

The invention claimed is:

1. A service system in the field of collecting human breast milk or in the field of medical drainage, wherein the system has a base unit assigned to an individual or an entity and at least one mobile data medium,
wherein the at least one mobile data medium can be brought by a user into data-communicating connection on the one hand with various products in the field and on the other hand with the base unit, wherein the at least one mobile data medium comprises data about operating parameters of a suction pump being a first of said various products which can be used by the at least one mobile data medium in a data- communication connection with a second of said various products, and
wherein the base unit can be brought by the user into communicating connection with an external information and data platform.

2. The service system according to claim 1, wherein the system comprises the external information and data platform and a plurality of base units, and wherein this information and data platform makes data at least one of exchangeable, convertible and optimizable and wherein this information and data platform makes the base units reassignable, wherein the data relate to at least one of the following areas: breast pumps for pumping human breast milk , drainage pumps, suction pumps in general; breast milk; treating breast milk; baby feeding; breast milk management; milk storage.

3. The service system according to claim 1, wherein the mobility of the mobile data medium is independent of at least one of the base unit of the products.

4. The service system according to claim 1, wherein the mobile data medium can be brought by the user into data-communicating connection with products from the field.

5. The service system according to claim 1, wherein the products comprise suction pumps.

6. The service system according to claim 5, wherein the suction pumps are breast pumps for pumping human breast milk.

7. The service system according to claim 5, wherein the suction pumps are thoracic drainage pumps.

8. The service system according to claim 5, wherein the suction pumps are wound drainage pumps.

9. The service system according to claim 1, wherein the external information and data platform is Internet-based.

10. The service system according to claim 1, wherein the external information and data platform is at least partly located in a cloud.

11. The service system according to claim 1, wherein the mobile data medium allows bidirectional data transfer with the base unit.

12. The service system according to claim 1, wherein the data communication between the mobile data medium and the base unit and/or between the mobile data medium and the suction pump takes place wirelessly.

13. The service system according to claim 1, wherein the base unit is an independent unit with an Internet connection function or part of a multifunctional communication means.

14. The service system according to claim 13, wherein the base unit is a smartphone.

15. The service system according to claim 1, wherein the base unit allows bidirectional information and data transfer with at least one region of the external information and data platform.

16. The service system according to claim 1, wherein the base unit can be brought by the user into data-communicating connection with the products.

17. The service system according to claim 1, wherein the base unit has a support surface for supporting the mobile data medium for the purpose of data transfer.

18. The service system according to claim 1, wherein the at least one mobile data medium has at least one sensor for the detection of measurement values.

19. The service system according to claim 1, wherein the at least one mobile data medium is formed for fastening on one of the products for the purpose of data-communicating or measurement value-detecting connection.

20. The service system according to claim 1, wherein the at least one mobile data medium has an external shape of one of a flat round gaming chip, a circular coin or a rectangular credit card.

21. The service system according to claim 1, wherein at least one of the first and the second of the various products is formed in order to receive the mobile data medium for the purpose of data-communicating or measurement value-detecting connection.

22. The service system according to claim 1, wherein at least one of the first and the second of the various products is shaped in order to receive the mobile data medium for the purpose of data-communicating or measurement value-detecting connection.

23. The service system according to claim 1, wherein the data communication between the mobile data medium and the base unit takes place wirelessly.

24. The service system according to claim 1, wherein the data communication between the mobile data medium and the suction pump takes place wirelessly.

* * * * *

UNITED STATES PATENT AND TRADEMARK OFFICE
CERTIFICATE OF CORRECTION

PATENT NO. : 10,091,302 B2
APPLICATION NO. : 15/123483
DATED : October 2, 2018
INVENTOR(S) : Matthias Haas et al.

Page 1 of 1

It is certified that error appears in the above-identified patent and that said Letters Patent is hereby corrected as shown below:

In the Specification

In Column 2, Lines 27-29, delete ", by a base unit having the features of Patent claim 14, a mobile data medium having the features of Patent claim 15".

In Column 2, Line 30, delete "18" and insert -- 19 --.

In the Claims

In Column 11, Line 41, after "least one of the base unit", insert -- and --.

Signed and Sealed this
Fourth Day of August, 2020

Andrei Iancu
*Director of the United States Patent and Trademark Office*